(12) United States Patent
Howard et al.

(10) Patent No.: US 10,893,896 B2
(45) Date of Patent: Jan. 19, 2021

(54) CRANIOPLASTY PLATE ASSEMBLY WITH PIVOTAL STRUTS

(71) Applicants: University of Iowa Research Foundation, Iowa City, IA (US); Karl Leibinger Medizintechnik GMBH & Co. KG, Muehlheim (DE)

(72) Inventors: Matthew A. Howard, Iowa City, IA (US); Axel Waizenegger, Muehlheim (DE)

(73) Assignees: University of Iowa Research Foundation, Iowa City, IA (US); Karl Leibinger Medizintechnik GMBH & Co. KG, Muehlheim (DE)

( * ) Notice: Subject to any disclaimer, the term of this patent is extended or adjusted under 35 U.S.C. 154(b) by 134 days.

(21) Appl. No.: 16/301,655

(22) PCT Filed: May 18, 2017

(86) PCT No.: PCT/US2017/033274
§ 371 (c)(1),
(2) Date: Nov. 14, 2018

(87) PCT Pub. No.: WO2017/201253
PCT Pub. Date: Nov. 23, 2017

(65) Prior Publication Data
US 2019/0282282 A1 Sep. 19, 2019

Related U.S. Application Data

(60) Provisional application No. 62/338,120, filed on May 18, 2016.

(51) Int. Cl.
*A61F 2/28* (2006.01)
*A61B 17/80* (2006.01)
(Continued)

(52) U.S. Cl.
CPC ........ *A61B 17/8061* (2013.01); *A61B 17/688* (2013.01); *A61F 2/2875* (2013.01);
(Continued)

(58) Field of Classification Search
CPC .................... A61F 2/688; A61F 2/2875; A61F 2002/30462; A61F 2002/30471;
(Continued)

(56) References Cited

U.S. PATENT DOCUMENTS 5,628,748 A 5/1997 Vicari
5,814,048 A 9/1998 Morgan
(Continued)

FOREIGN PATENT DOCUMENTS

WO 2014176437 A2 10/2014

OTHER PUBLICATIONS

PCT/US2017/033274, University of Iowa Research Foundation, International Search Report and Written Opinion, dated Sep. 21, 2017.

*Primary Examiner* — Suba Ganesan
*Assistant Examiner* — Aren Patel
(74) *Attorney, Agent, or Firm* — Thomas C. Saitta

(57) ABSTRACT

An adjustable cranioplasty plate assembly is provided for use following a craniectomy. The assembly includes a ring which is attached to the skull around the skull opening and a plate adjustably mounted to the ring. The plate is moveable between a raised position spaced above the ring and a lower position substantially flush with the ring. The plurality of extendable and retractable struts extends between the ring and the plate to provide the plate adjustability. The plurality of stay cables extending between the ring and the plate provide lateral stability in the raised position. The assembly replaces the native bone and eliminates the need for subsequent cranioplasty surgery. In one embodiment, the plate
(Continued)

includes a rigid central portion, three rigid mounting tabs, and a plurality of malleable tapered perimeter petals which provide a smooth interface between the plate and the skull of the patient.

18 Claims, 15 Drawing Sheets

(51) Int. Cl.
*A61B 17/68* (2006.01)
*A61F 2/30* (2006.01)
*A61F 2/48* (2006.01)

(52) U.S. Cl.
CPC .............. *A61F 2002/3052* (2013.01); *A61F 2002/30462* (2013.01); *A61F 2002/30471* (2013.01); *A61F 2002/30537* (2013.01); *A61F 2002/30578* (2013.01); *A61F 2002/482* (2013.01)

(58) Field of Classification Search
CPC .... A61F 2002/3052; A61F 2002/30537; A61F 2002/30578; A61F 2002/482; A61B 17/8061; A61B 17/8071

USPC ..................................... 623/17, 19
See application file for complete search history.

(56) References Cited

U.S. PATENT DOCUMENTS

| | | |
|---|---|---|
| 6,350,284 B1 | 2/2002 | Tormala et al. |
| 2006/0259040 A1 | 11/2006 | Wellisz et al. |
| 2007/0173844 A1 | 7/2007 | Ralph et al. |
| 2007/0191848 A1 | 8/2007 | Wack et al. |
| 2008/0200954 A1 | 8/2008 | Tucci |
| 2008/0208347 A1 | 8/2008 | Muratoglu |
| 2010/0256641 A1 | 10/2010 | Rabiner et al. |
| 2012/0184999 A1 | 7/2012 | Khanna |
| 2012/0259344 A1 | 10/2012 | Johnston, Jr. |
| 2013/0158670 A1* | 6/2013 | Tigno, Jr. .............. A61F 2/2875 623/17.19 |
| 2017/0239054 A1* | 8/2017 | Engstrand ........... A61F 2/30965 |
| 2017/0273794 A1 | 9/2017 | Howard |
| 2017/0079685 A1 | 12/2017 | Dirisio |

* cited by examiner

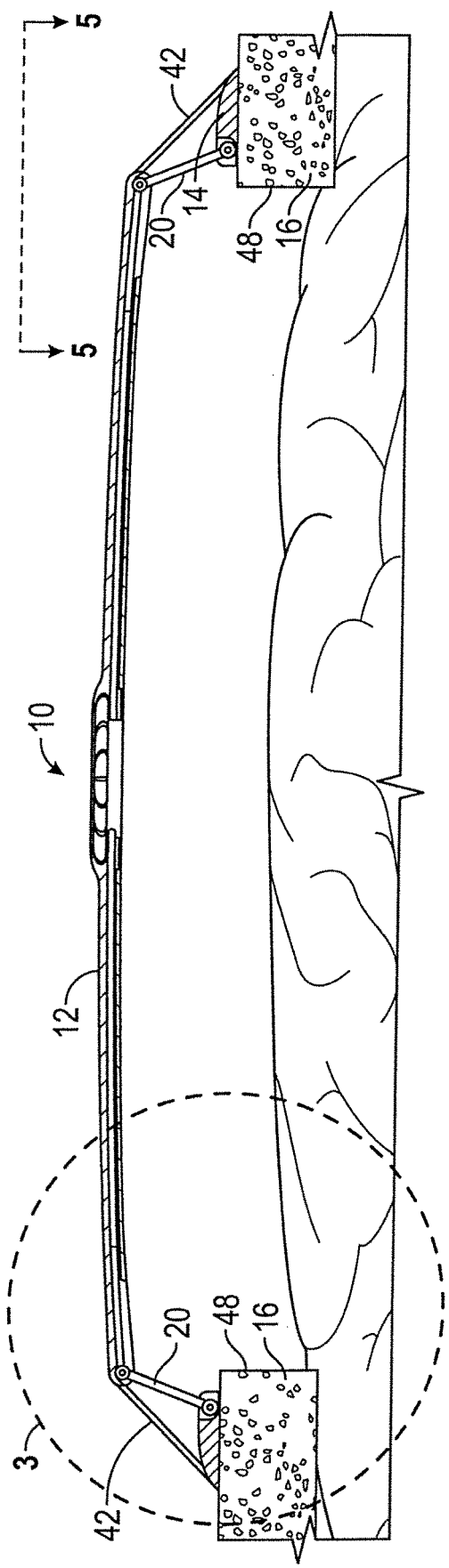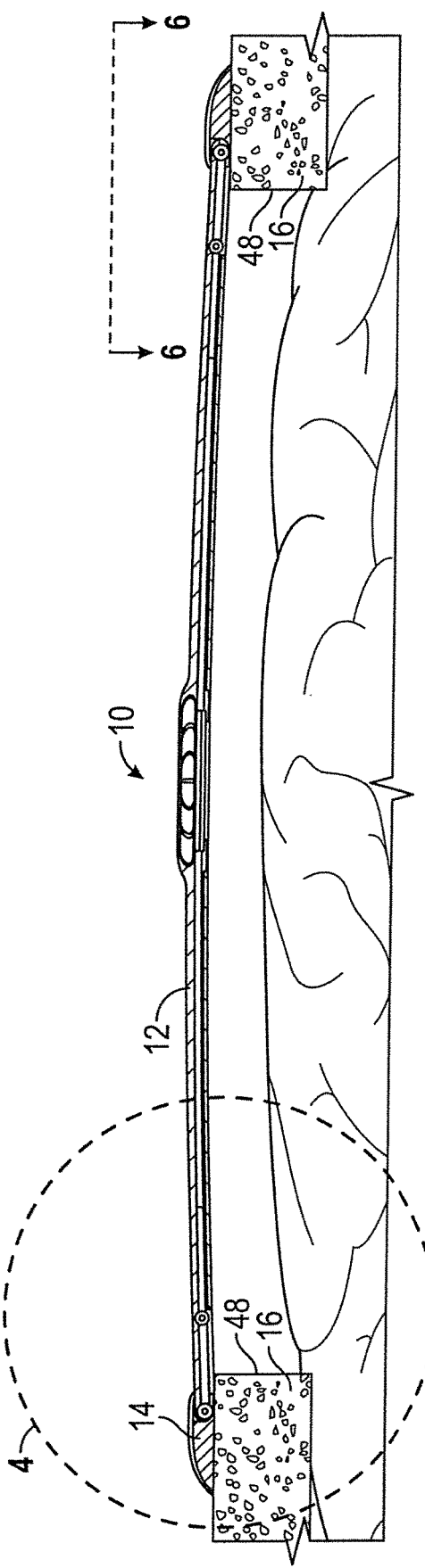

CRANIOPLASTY PLATE ASSEMBLY WITH PIVOTAL STRUTS

CROSS-REFERENCE TO RELATED APPLICATIONS

This claims priority to Provisional Application U.S. Ser. No. 62/338,120, filed on May 18, 2016, which is herein incorporated by reference in its entirety.

BACKGROUND OF THE INVENTION

A craniectomy is a medical surgical procedure commonly performed to manage intractable brain swelling, often caused by trauma or stroke. When a patient is managed using a standard craniectomy procedure, two surgeries are required. First, a craniectomy is performed, wherein a section of the skull is removed and then the skin or scalp is closed over the skull opening. The craniectomy allows for the brain tissue to expand through the opening to reduce intracranial pressure. After the brain swelling has receded, which may take several weeks or months, a second cranioplasty operation is required to replace the saved native bone material, or alternatively, to implant a prosthetic skull piece, such as a thin titanium skull plate. This second operation restores a solid covering over the skull opening or defect.

The removal of the skull section in the craniectomy allows the brain tissue to expand without restriction by the skull. Without the skull protection, the brain is vulnerable under the skin until swelling reduces in the following weeks or months, until the cranioplasty surgery takes place to repair the skull defect. During the interim between the craniectomy and the cranioplasty procedures, the patient normally wears a helmet to protect the brain. The cranioplasty surgery increases the high costs associated with patient care. The cranioplasty procedure also increases the patient risk, with potential brain injury from the significant manipulation of the brain which can cause intracranial hemorrhage and seizures, increased risk of infection, and wound breakdown. Also, prior to the cranioplasty, patients often develop headaches and have delays in their recovery due to the loss of normal intracranial pressure gradient provided by the skull.

Therefore, a primary objective of the present invention is the provision of a craniectomy surgical procedure which achieves both the decompression and relief of intracranial pressure and a protective solid covering over the skull opening, with only one surgical operation.

Another objective of the present invention is a provision of an improved cranial plate assembly for use after a craniectomy.

A further objective of the present invention is a provision of a cranial plate assembly having a plurality of adjustable struts to position the plate above the skull.

Yet another objective of the present invention is a provision of a cranial plate assembly which can be implanted during a craniectomy operation, without the need for a follow up cranioplasty operation.

Another objective of the present invention is a provision of a surgical procedure wherein a portion of the skull is removed to expose the brain, and a plate is positioned over the skull, in the appropriate spatial relationship to the skull defect, and then after brain swelling recedes, the plate is lowered to a position adjacent or flush with the skull, without a second surgical procedure.

Still another objective of the present invention is the provision of a cranioplasty plate assembly which is adjustably positioned on a patient's skull.

Another objective of the present invention is a provision of a cranioplasty plate assembly which can be raised and lowered relative to the skull.

Yet another objective of the present invention is a provision of a cranioplasty plate assembly having contraction members for controlling the position of the plate over a skull opening.

A further objective of the present invention is a provision of a cranioplasty plate assembly having means for preventing lateral displacement of the plate.

Still another objective of the present invention is a provision of a cranioplasty plate assembly which can be selectively positioned and maintained over a skull opening.

Another objective of the present invention is the provision of a method for protecting the brain following removal of a portion of the skull wherein a ring is fixed to the skull and a plate is adjustably attached to the ring to accommodate brain swelling.

Yet another objective of the present invention is the provision of a cranial plate having a three-point fixation to the skull and having a plate with a rigid central portion, three rigid mounting extensions, and malleable tabs or petals.

Another objective of the present invention is the provision of a cranial plate which is substantially flush with the skull surface when in a lowered position after brain swelling has receded.

A further objective of the present invention is a provision of the improved cranial plate assembly which is economical to manufacture, simple to implant, and safe for the patient.

These and other objectives have become apparent from the following description.

SUMMARY OF THE INVENTION

The cranioplasty plate assembly of the present invention includes a ring adapted to be fixed to the skull around a skull opening following a craniectomy surgery. A cranioplasty plate is adjustably mounted to the ring using a plurality of struts and stay cables extending radially outwardly between the plate and the ring. The struts are moveable between an extended position which raises the plates relative to the ring and a retracted position which lowers the plate relative to the ring. The plate is initially maintained at a spaced distance above the skull to protect the brain. The struts are pivotally attached to the ring and slidably mounted to the plate. The position of the struts can be adjusted via a ratchet wheel or by a small electric motor.

The cranioplasty plate assembly, eliminates the need for cranioplasty surgery after brain swelling has receded. After the brain swelling completely resides, the plate can be lowered to a position adjacent or flush with the skull, without the need to replace the native bone.

In a preferred embodiment, the cranioplasty plate of the present invention is fixed to the skull at three equal-distant points. This preferred cranial plate has a rigid central portion and three rigid mounting tabs for attachment to the skull. Between the mounting tabs, at the perimeter of the plate, are malleable petals or tabs which are initially bent or angled downwardly toward the skull when a plate is in an initial raised position, and then extended substantially flat so as to be flush with the skull surface when the plate is in the lowered position, so as to provide a smooth interface between the plate and the skull surface.

BRIEF DESCRIPTION OF THE DRAWINGS

FIG. 1 is a side elevation view of a cranial plate according to the present invention in a raised position.

FIG. 2 is a side elevation of the plate in a lowered position.

DETAILED DESCRIPTION OF THE INVENTION

Figure 3:
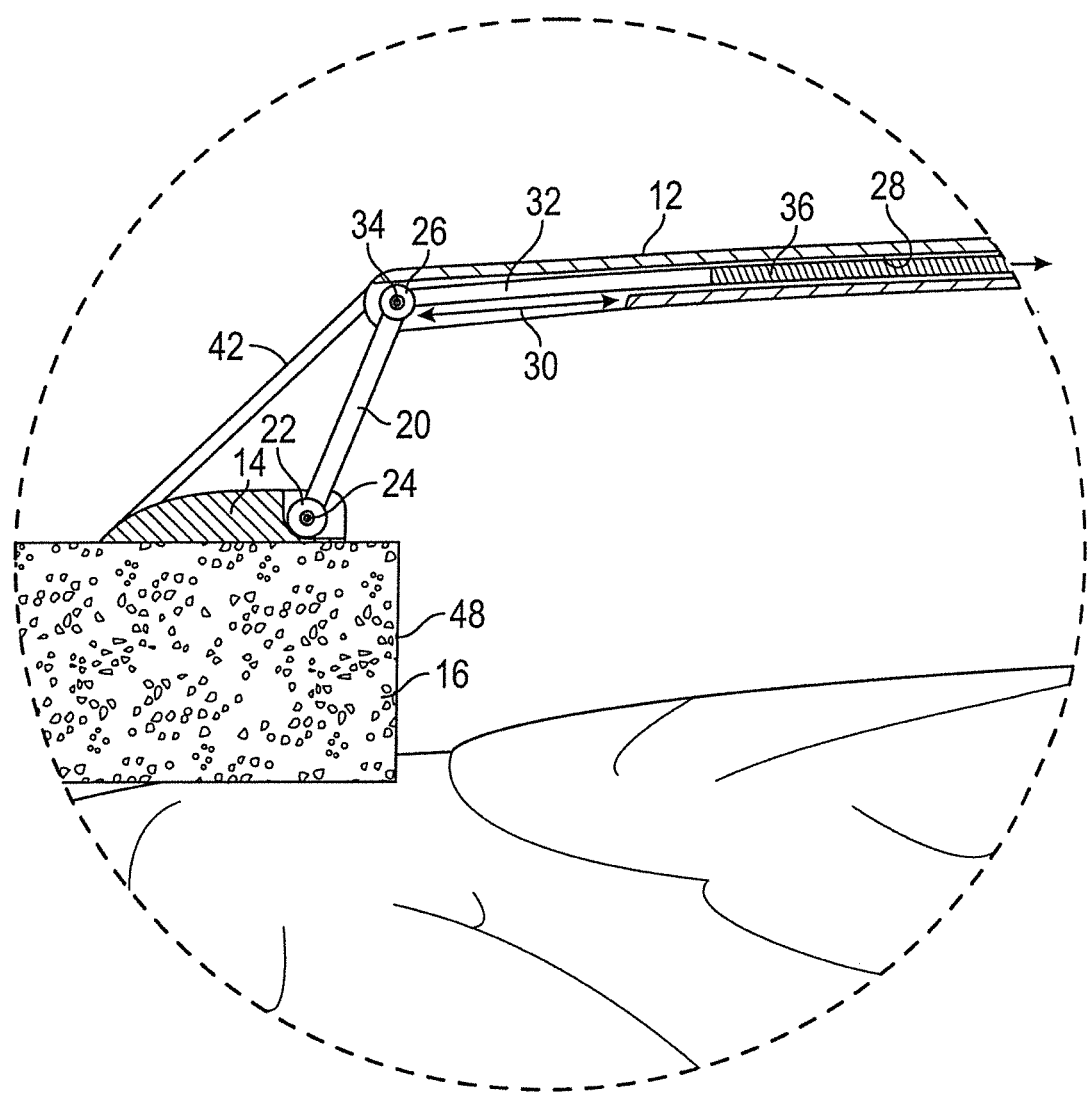
FIG. 3 is an enlarged partial sectional view showing the pivotal elevation strut, contraction structure, and stay cable, in a raised position, as taken along line 3-3 of FIG. 1.

The present invention is directed towards a cranial plate assembly and method of surgically installing the assembly during a craniectomy neurosurgical procedure. The plate assembly is intended to replace the skull bone removed during the craniectomy, and eliminates the need for a follow up cranioplasty surgery, to replace the native bone.

The cranial plate assembly of the present invention is generally designated by the reference numeral 10 in the drawings. The assembly 10 includes a plate 12 and a ring 14. The ring 14 is secured to a patient's skull 16 using screws 18. The plate 12 is attached to the ring 14 with struts 20 spaced equally around the plate 12. While, the drawings show the use of twelve struts 20 spaced 30° apart, it is understood that more or less struts can be utilized, with a minimum of three struts spaced 120° apart.

Each strut 20 has an outer end 20 pivotally connected to the ring 14 by a pin 24. Alternatively, the outer end 22 of each strut 20 can be pivotally secured to the ring 14 in any other convenient manner, including an integrally formed hinge.

Figure 4:
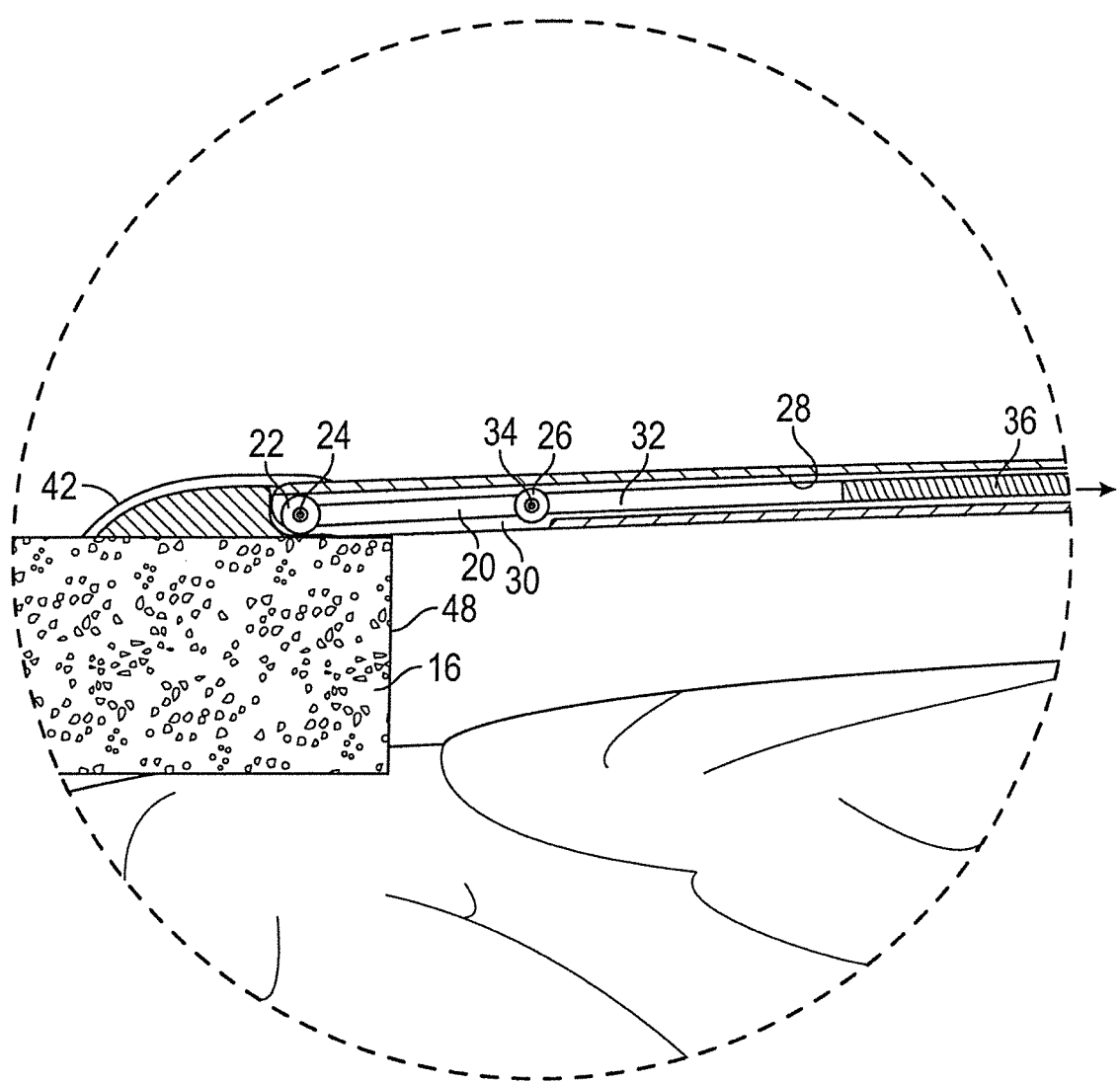
FIG. 4 is an enlarged partial sectional view taken along lines 4-4, FIG. 2.
Figure 5:
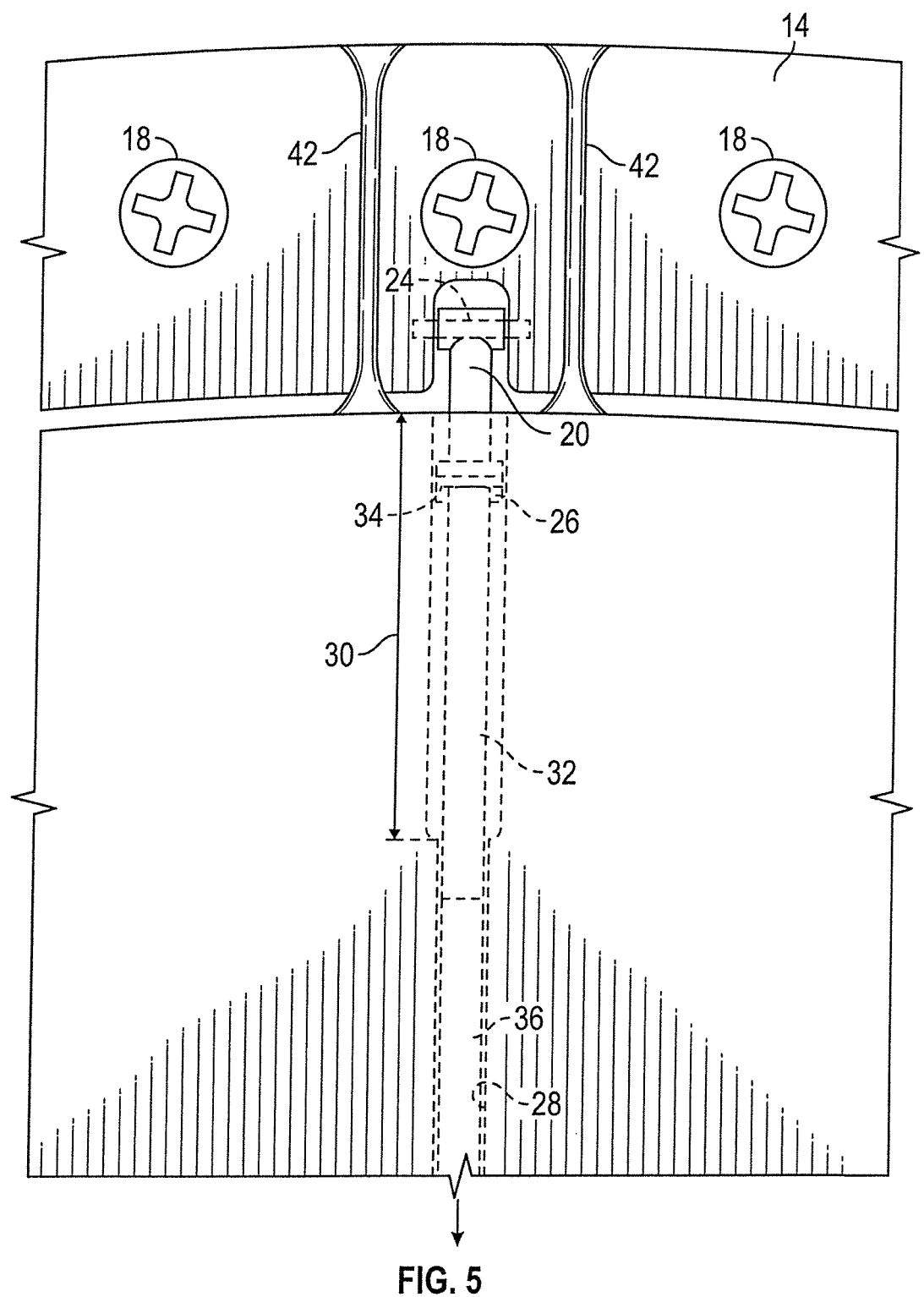
FIG. 5 is an enlarged partial top planned view of the assembly in the raised position, taken along lines 5-5 of FIG. 1.
Figure 8:
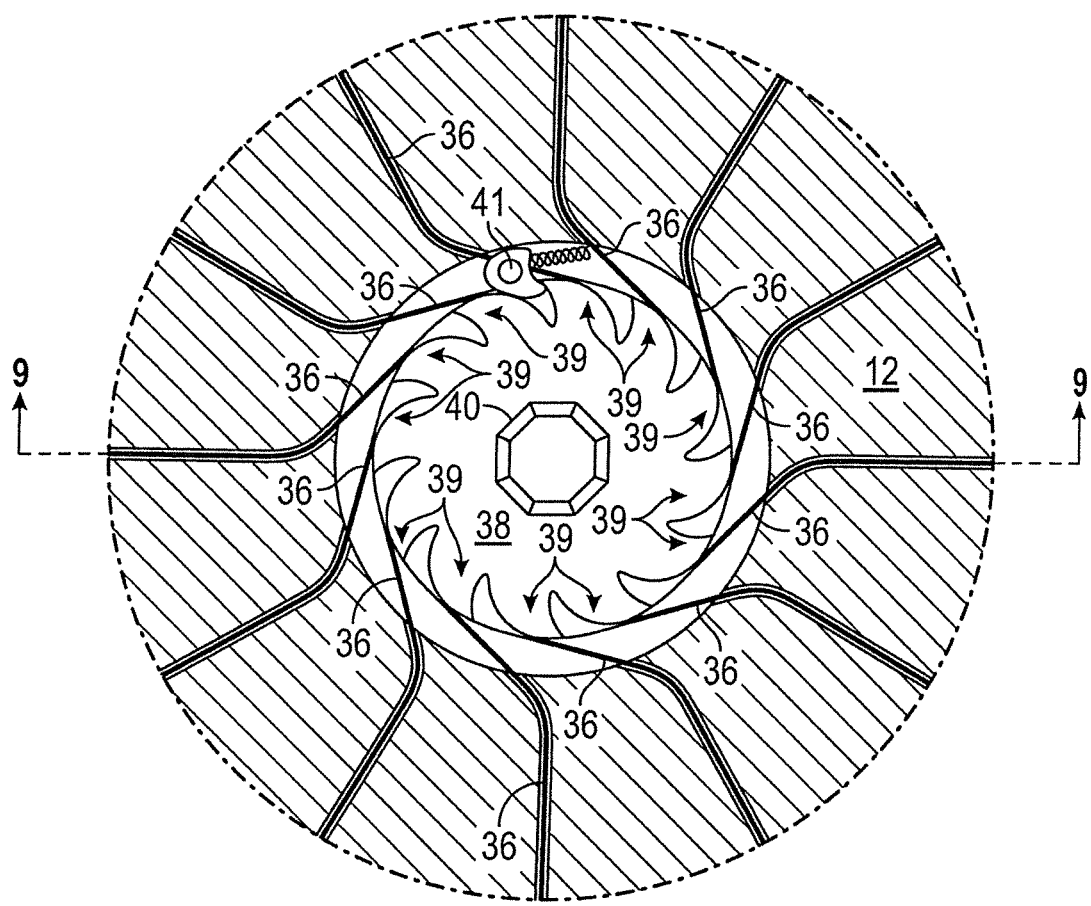
FIG. 8 is an enlarged top plan view of the circular ratchet of the assembly.
Figure 9:
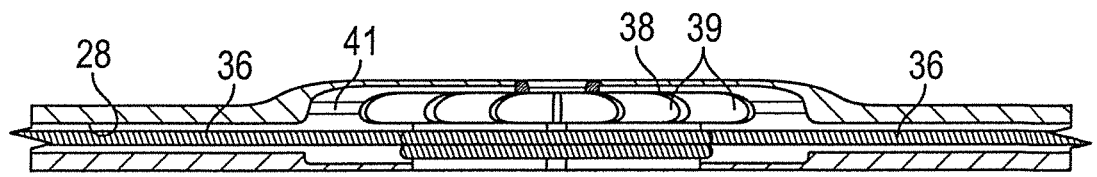
FIG. 9 is a sectional view of the ratchet taken along lines 9-9 of FIG. 8.
Figure 10:
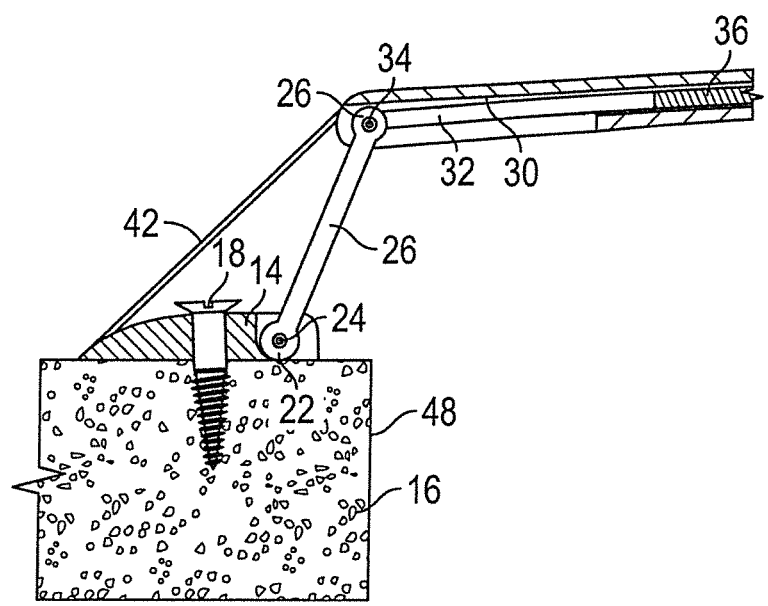
FIG. 10 is another enlarged side view of the strut in the raised position.
Figure 11:
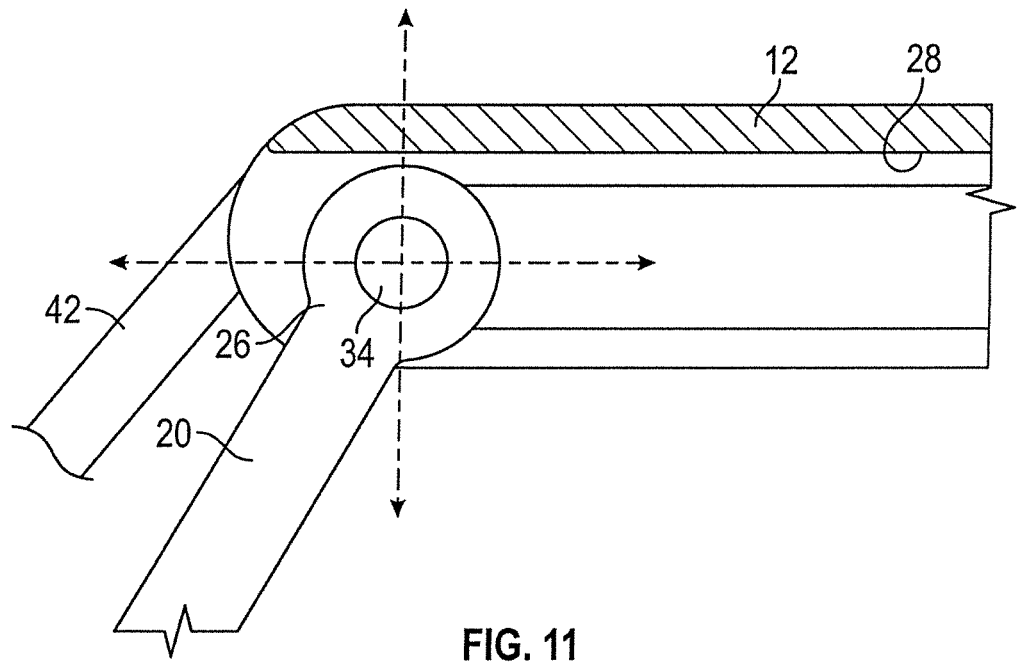
FIG. 11 is another enlarged side view of the strut in the raised position.
Figure 12:
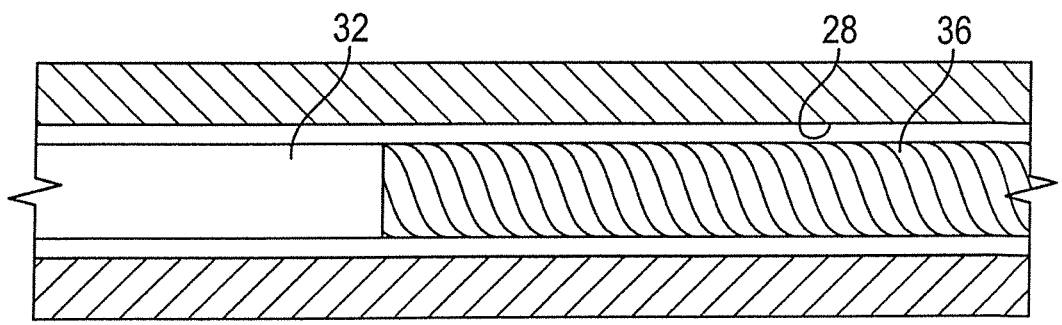
FIG. 12 is a partial sectional view of the contraction channel, rod and cable according to the present invention.
Figure 13:
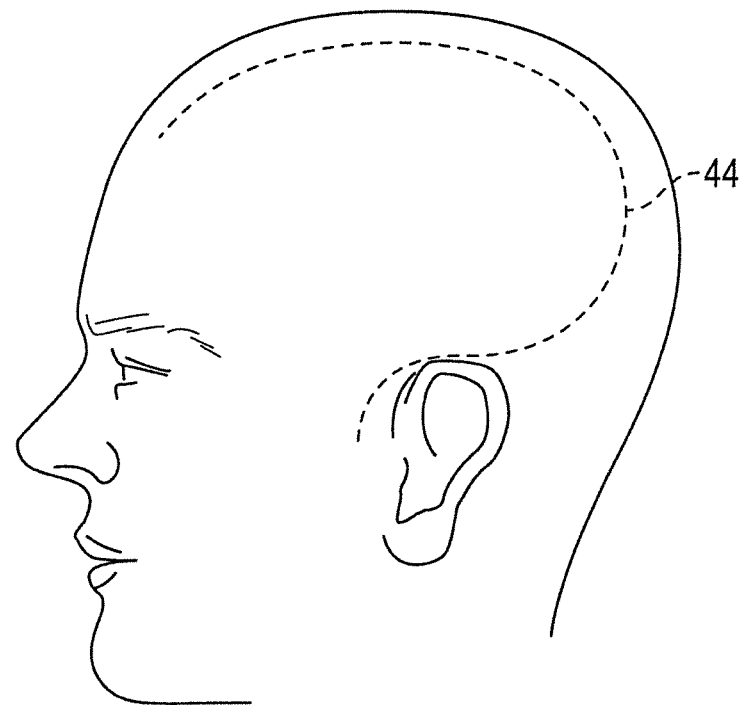
FIG. 13 is a side elevation view showing a person's head with a standard question mark shaped trauma flap of a craniotomy.

The inner end 26 of each strut 20 is captured in a channel 28 in the plate 12. A slot 30 extends along the bottom of the channel 28 so that the inner end 26 can slide within the channel. A rod or cylinder 32 is pivotally connected to the inner end 26 of the strut 20 via a pin 34. Alternatively, the rod 32 and the strut 20 can be integrally formed with a flexible hinge. The inner end of the rod 32 is attached to a wire or cable 36, which in turn is attached to a ratchet wheel or spool 38 mounted at the center of the plate 12. The struts 20, the rods 32, cables 36, and the ratchet wheel 38 form a contraction system whereby rotation of the ratchet wheel 38 pulls or draws the cables 36 and the rods 32 radially inwardly, such that the inner ends 26 of the struts 20 slide along the channel 28 via the slots 30. Thus, the plate 12 is moveable from a raised position spaced above the skull 16 (FIGS. 1, 3, and 5) to a lowered position adjacent to the skull (FIGS. 2, 4 and 6) upon actuation of the ratchet wheel 38. The ratchet wheel 38 includes a head 40 that can receive a wrench or socket for turning the ratchet wheel 38 in a clockwise motion in FIG. 8, when it is desired to lower the plate 12. The wheel 38 has a plurality of teeth 39, and a pawl catch 41 to engage one of the teeth, and prevent counter-rotation of the wheel 38.

Figure 6:
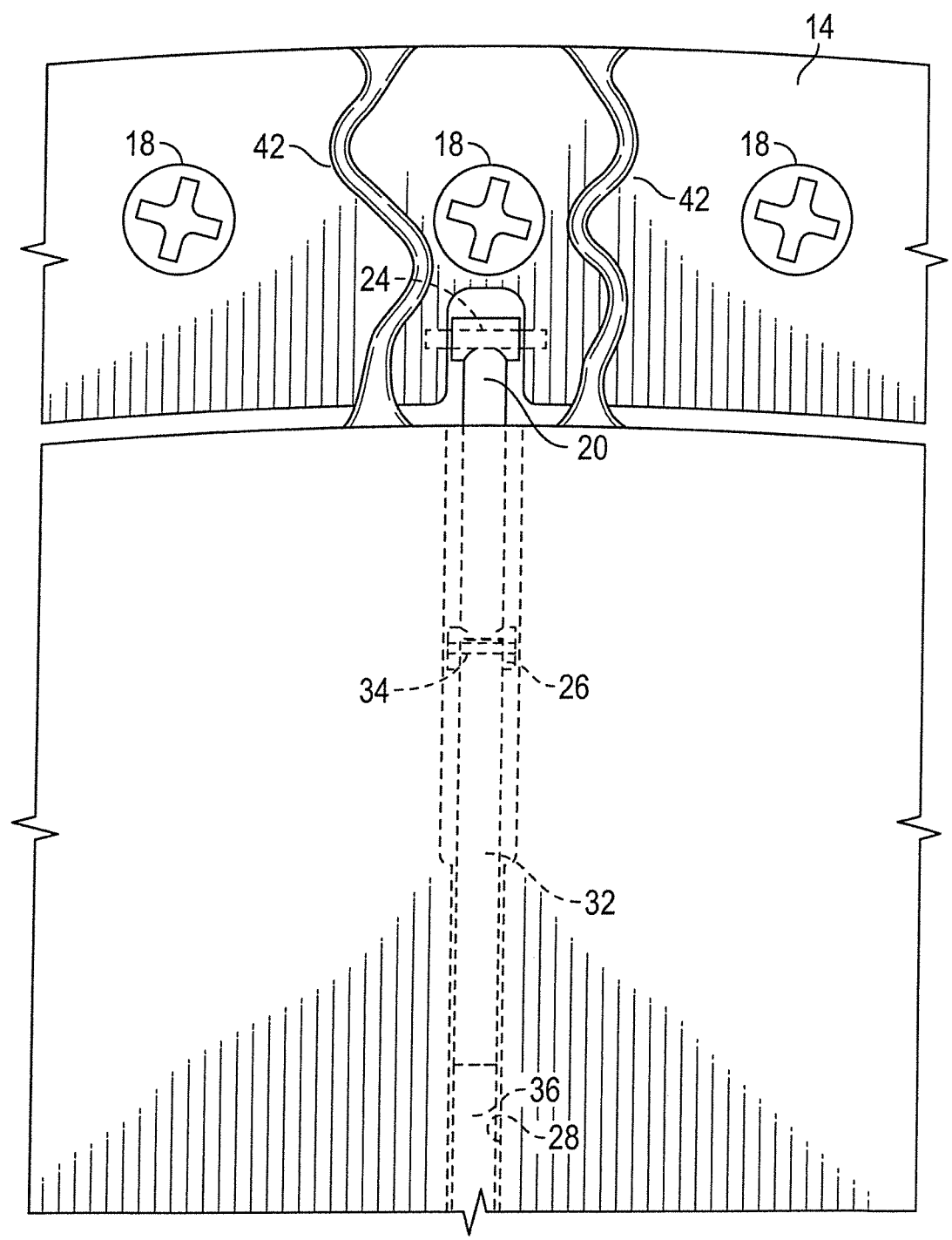
FIG. 6 is an enlarged partial top plan view of the assembly in the down position taken along lines 6-6 of FIG. 2.
Figure 7:
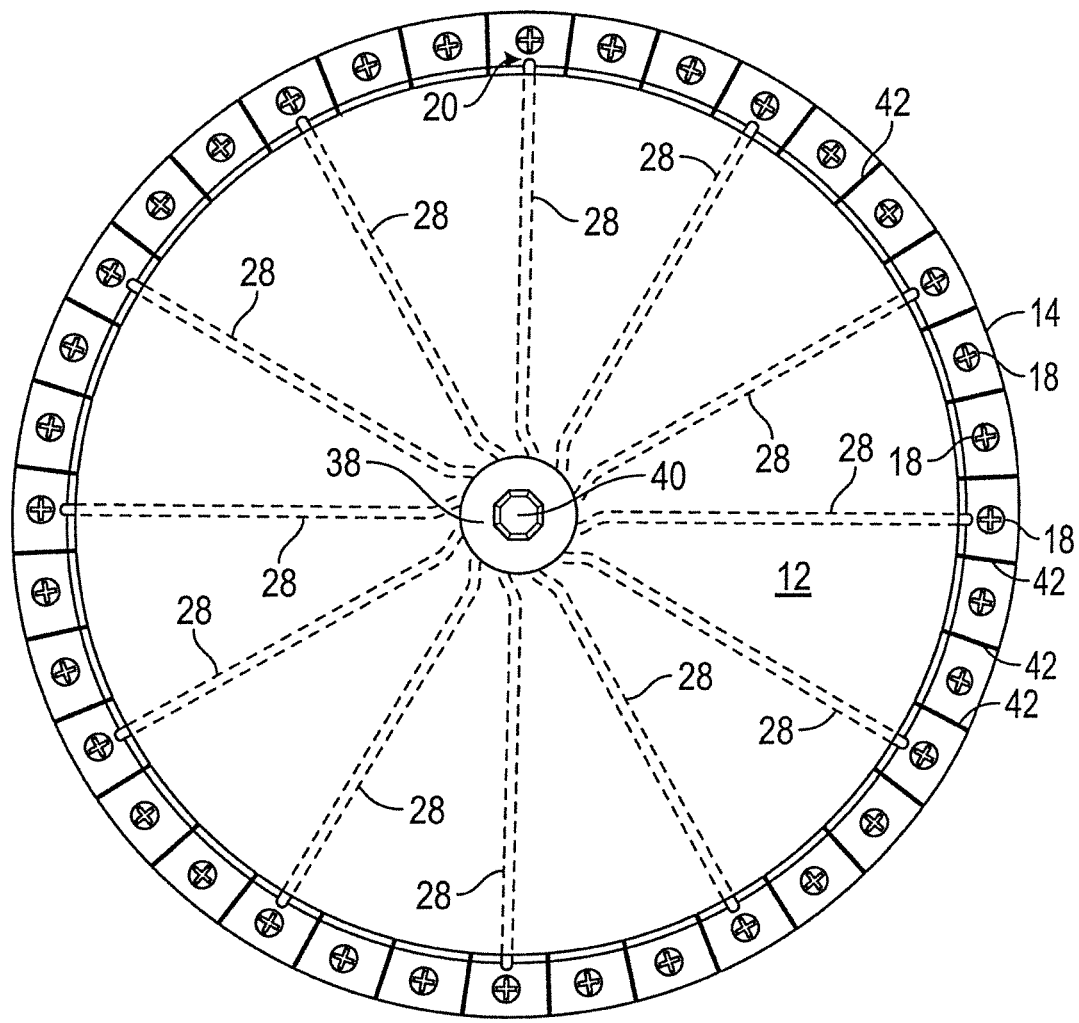
FIG. 7 is a top plan view of the assembly.

Stay cables 42 extend between the perimeter of the plate 12 and the ring 14 to keep the plate 12 centered when in the raised position, wherein the cables 42 are under tension. When the plate 12 is moved to the lowered position, the tension on the cables 42 is removed such that the cables 42 are slack (as shown in FIG. 6).

Figure 14:
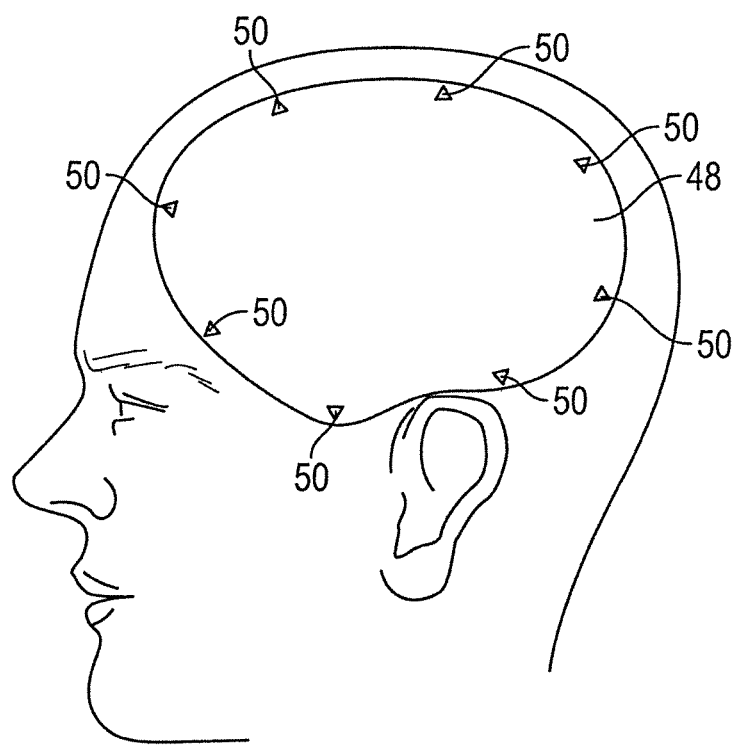
FIG. 14 is a side elevation view of a person's head showing the placement of a template for the cranial plate according to the present invention.
Figure 15:
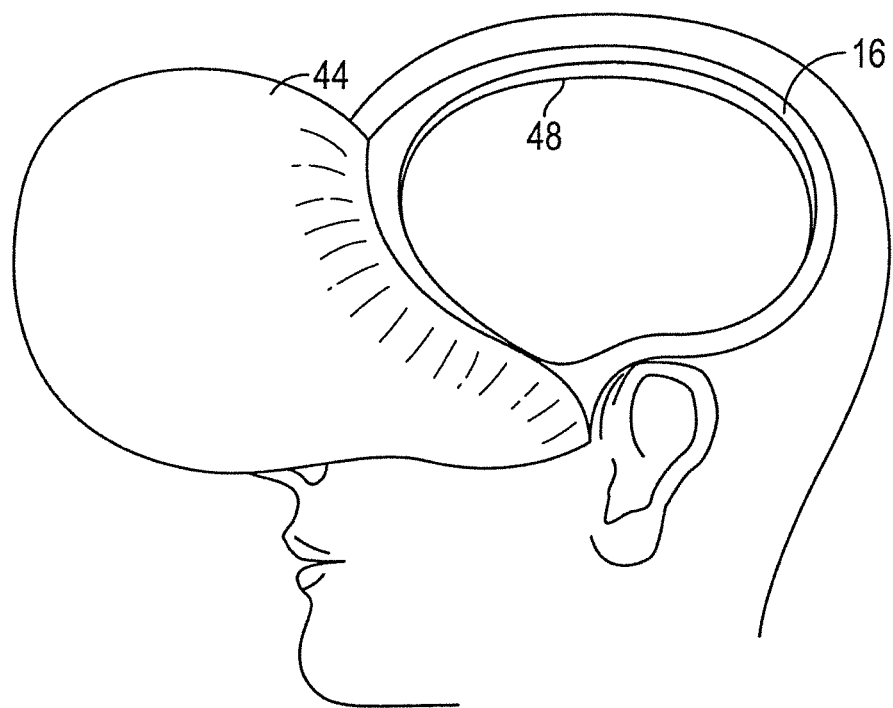
FIG. 15 is a side elevation view showing an opening in the skull after a portion of the skull is removed.
Figure 16:
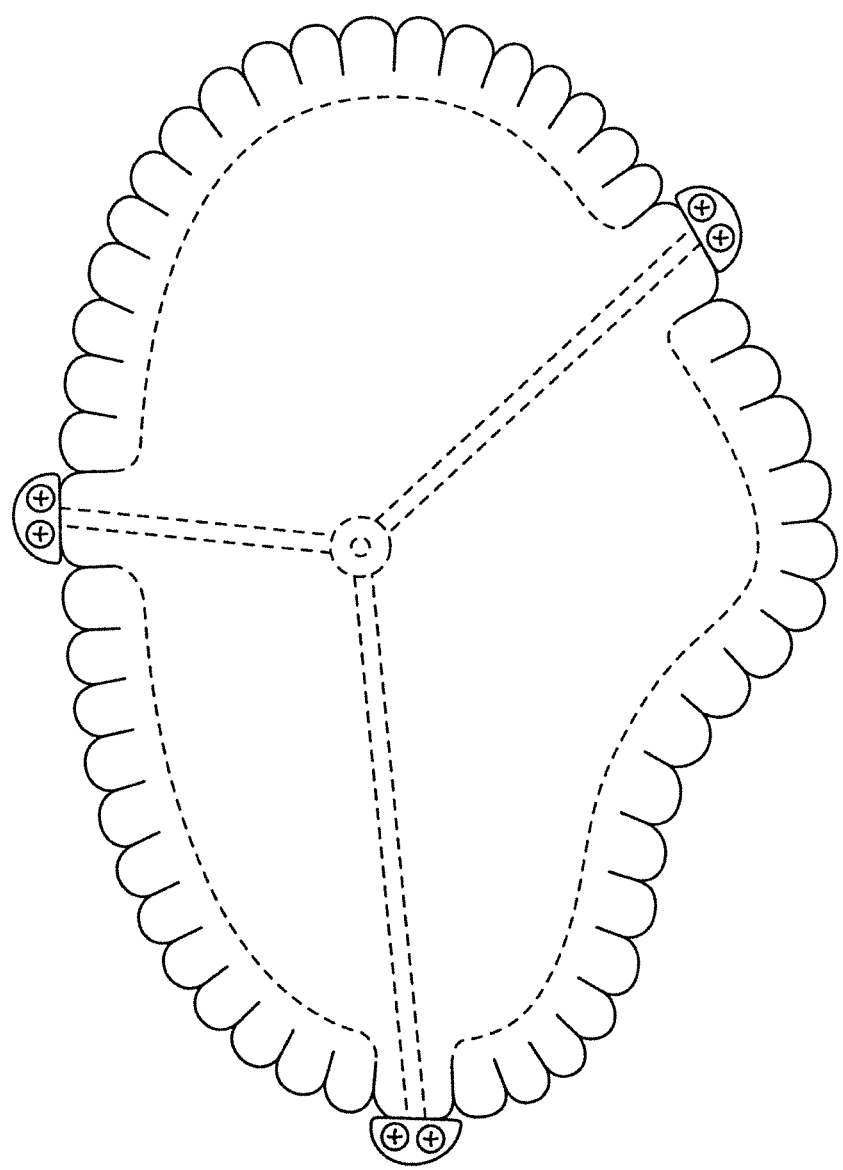
FIG. 16 is a top plan view of a preferred embodiment of the cranioplasty plate assembly according to the present invention, wherein the plate assembly is fixed at 3 points to the skull and has three struts for adjusting the plate assembly position between raised and lowered.

The neurosurgical method of the present invention involves first step of exposing the skull using a standard trauma flap 44 cut in the skin, as shown in FIG. 16. A template 46 is positioned over the skull opening 48 so that the surgeon or medical personnel can mark the boundary of the template 46 and the locations 50 for the fixture screws 18, as shown in FIG. 14. The template border defines the subsequent bone cut or cuts to be made by the surgeon. The template 46 is then removed.

Next, the surgeon performs the craniotomy, cutting the skull bone along the marked lines of the template to remove a portion of the skull, such that the skull opening 48 matches the template size and shape. Once the dura is opened, the brain is decompressed in standard fashion. Artificial dura may be placed over the exposed brain.

Then, the surgeon positions the cranioplasty plate 10 and ring 12 over the skull opening 48, such that the fixation points defined by screw holes in the ring 12 are aligned with the fixation location marks 50. The surgeon then installs standard cranial screws 18 through the ring holes to secure the cranioplasty ring 12 at the fixation points 50. The circumferential arrangement of the fasteners 18 around the perimeter edge of the ring 12 prevents displacement of the ring. The struts 20 and stay cables 42 ensure proper initial positioning of the plate 10 above the skull 16. The surgical procedure closes with the installation of a subgaleal drain (not shown) and closing of the skin flap 44 using staples or stitches.

Thus, the cranial plate assembly 10 includes a moveable plate 12 and the stationary fixation ring 14, with the contraction system allowing the plate to move between the up position, approximately 5 mm above the skull surface, and the down position adjacent or inside the skull opening 48 so as to be substantially flush with the skull 16. The struts 20 prevent the plate 12 from accidentally moving downwardly, while the stay cables 42 prevent the plate 12 from shifting laterally or upwardly from the initial up position. Thus, the combination of the struts 20 and stay cables 42 around the circumference of the assembly 10 maintains the stability of the assembly at all times. The contraction system comprising the struts 20, the rod or cylinder 32, the cable 36, and the channel 28 in the plate 12 controls and changes the position of the plate 12 relative to the skull 16 via the ratchet wheel 38. The guide channel 28 in the plate 12 also precludes accidental buckling or movement of the plate, for example, if the plate is bumped or otherwise inadvertently contacted.

Preferably, the ratchet wheel 38 and the head 40 are covered by the skin flap 44. When brain swelling has abated, and it is time to lower the plate 12, a small incision can be made in the skin flap 44 to provide access to the ratchet head 40, thereby allowing the ratchet wheel 38 to be rotated to retract the cables 36 and rods 32 so as to be pull the connected struts 20 towards the center of the plate 12, and thereby lower the plate 12. The incision can then be closed with one or more sutures or an adhesive.

The plate assembly 10 provides the ability to adjustably select and set the position of the plate 12 above the skull via the contraction system. More particularly, the interface points between the struts 20 and the ring 14 and the plate 12 are constrained above the dorsal surface of the guide channels 28. Lateral displacement of the interface points is prevented by the side walls of the guide channels 28, while downward or ventral displacement of the interface points is prevented by the rods or cylinders 32 which are fully circumferentially enclosed at their inner ends by the guide channels 28. Displacement toward the lateral or perimeter edge of the plate 12 is prevented by a perimeter lip 52 on the plate 12, and because the contraction system cannot be stretched. Similarly, displacement towards the center of the plate 12 is prevented because the contract system cannot be compressed. The only manner in which the interface position of the struts 20 and contraction system can be adjusted is by reeling in the cables 36 using the ratchet wheel 38.

In the preferred embodiment, the guide channels 28 are formed within the plate 12, but alternatively can be attached on the bottom or the top of the plate.

As an alternative to the ratchet wheel 38, a small electric drive motor can be mounted on the plate 12 and attached to the cables 36, and actuated with the remote control device which would eliminate the minor surgical incision required for access to the ratchet head 40. Other actuators to adjust the plate position are also within the scope of the invention.

Thus, the cranioplasty plate assembly 10 of the present invention eliminates the standard second cranioplasty surgical procedure conventionally required for these patients.

In a preferred embodiment, all of the components of the assembly 10 are made from rigid and light weight material such as metal, plastic or composites. The plate 12 and/or the ring 12 may include holes or openings to minimize the weight, without sacrificing strength and durability. Also, other types of linear actuators can be substituted for the contraction system to raise and lower the plate 12.

A preferred embodiment of the cranioplasty plate assembly is shown in FIGS. 16-21. This preferred assembly 10A includes a plate 12A with three struts 20A and a central ratchet wheel 38A which function as described above with respect to the cranioplasty plate assembly 10. The ring 14 described above is replaced with 3 separate mounting blocks 54 which are fixed to the skull adjacent to the skull opening using screws 18. The plate 10A has a rigid central portion 56 and three rigid mounting tabs or extensions 58 to which the struts 20A extend. The perimeter edge of the plate 12A has malleable flange petals or tabs 58 between the mounting tabs 56, as seen in FIG. 16. The petals 58 are tapered to a relatively thin thickness of their outer edges.

Figure 17A:
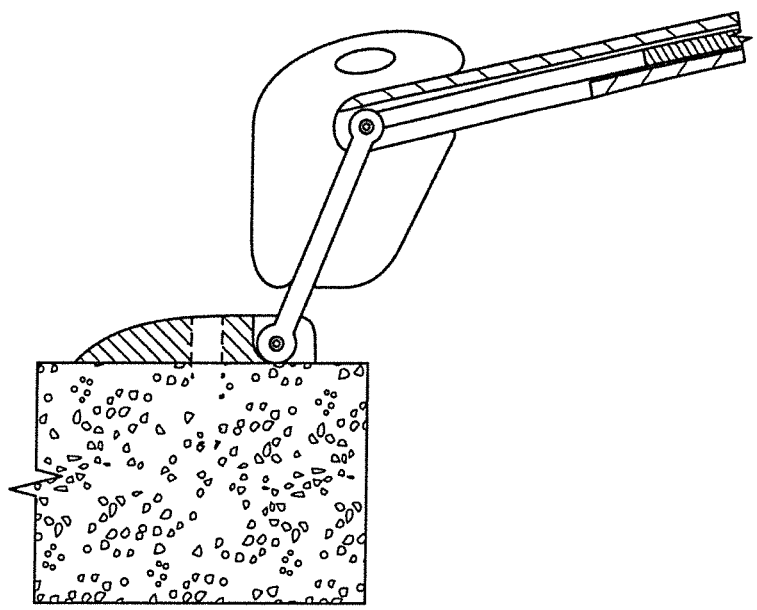
FIG. 17A is a side elevation view of one edge of the plate assembly shown in FIG. 16, including the mounting block and strut block, with the strut in an extended position so that the plate assembly is in a raised position.
Figure 17B:
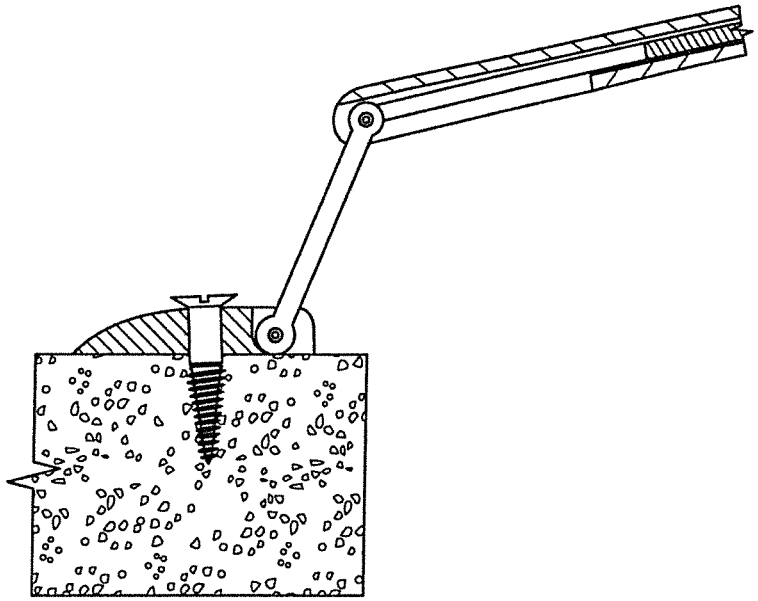
FIG. 17B is a view similar to 17A, with the strut block removed following installation of the plate assembly to the skull.
Figure 17C:
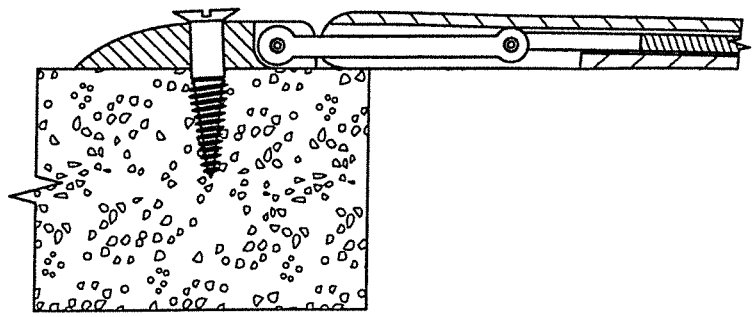
FIG. 17C is another side elevation view showing the plate of FIG. 16 in a lowered position after brain swelling has resided.
Figure 18A:
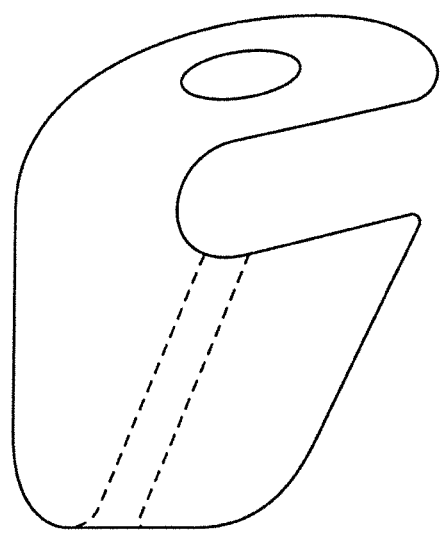
FIG. 18A is a side elevation view of the strut block.
Figure 18B:
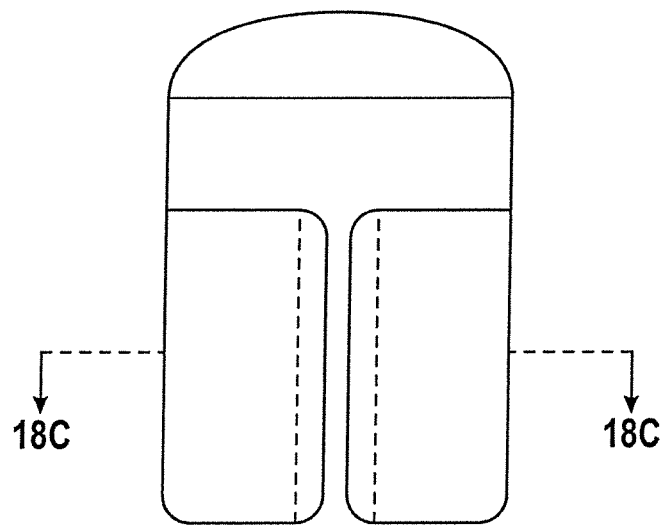
FIG. 18B is a front elevation view of the strut block.
Figure 18C:
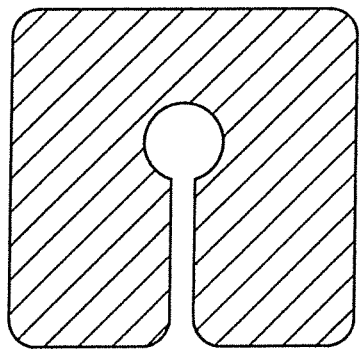
FIG. 18C is a sectional view of the strut block taken along lines C-C of FIG. 18B.

When installing the cranioplasty plate assembly 10A under the patient's skull, the mounting blocks 54 are attached to the skull 16 at the desired locations using the screws 18. The strut blocks 60 hold the struts 20A in an inclined position with the plate 12A spaced above the skull 48, as seen in FIG. 17A. After the assembly 10A is installed, the strut blocks 54 are removed, and the plate remains in the raised position, as seen in FIG. 17B. After skull swelling has receded, the plate can be lowered to a position substantially flush with the skull 16, as shown in FIG. 17C, be actuating the ratchet wheel 38A such that the rods 32A and cables 32A, 36A retract and lower the plate 12A, similar to the procedure described above with respect to the plate assembly 10.

Figure 19A:
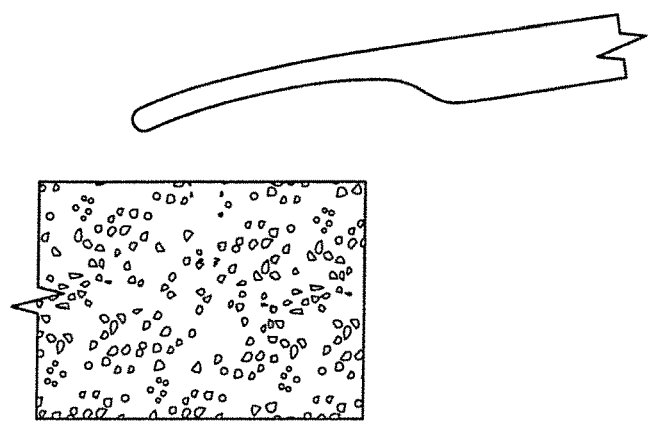
FIG. 19A is a side elevation view showing the plate of FIG. 16 in a raised position and the malleable flange petals curved downwardly toward the skull (and with the strut removed for clarity).
Figure 19B:
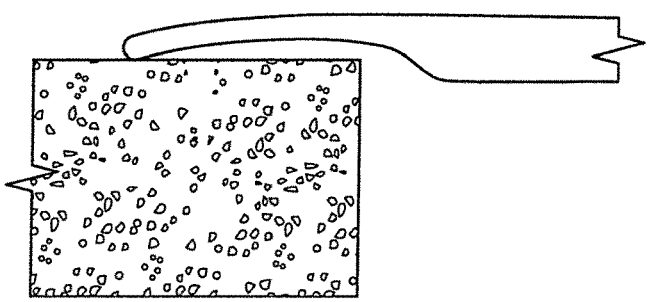
FIG. 19B is a side elevation view showing the plate of FIG. 16 in a lowered position and the malleable flange petals substantially flush with the skull.
Figure 20A:
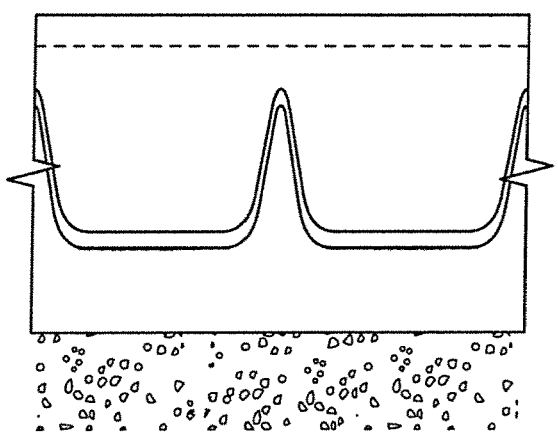
FIG. 20A is a side elevation view of a portion of the perimeter edge of the plate of FIG. 16, with the plate in a raised position and the malleable flange petals bent downwardly toward the skull.
Figure 20B:
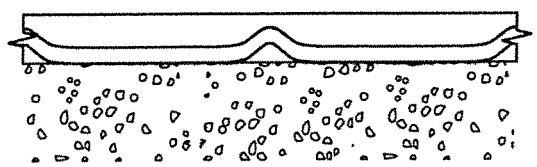
FIG. 20B is a side elevation view showing the plate in a lowered position and the petals substantially flush with skull.
Figure 21A:
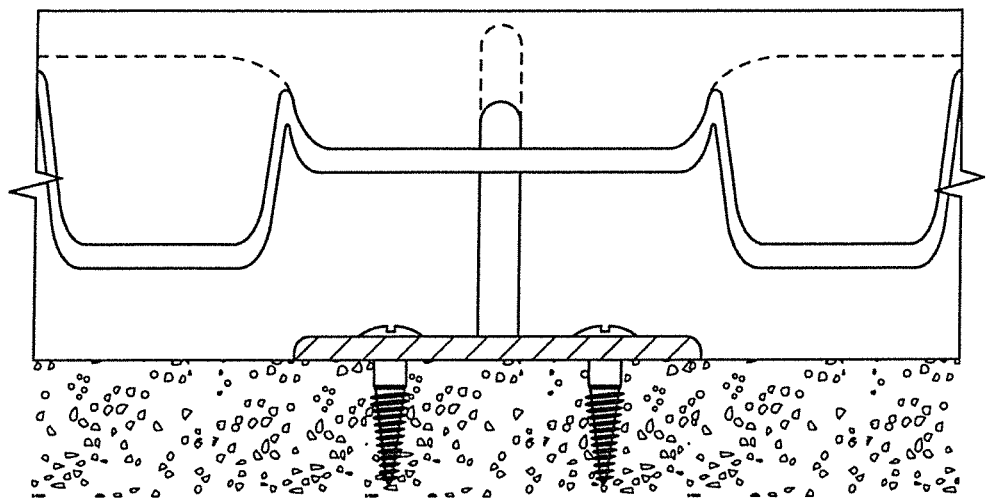
FIG. 21A is another side elevation view showing the plate of FIG. 16 in a raised position.
Figure 21B:
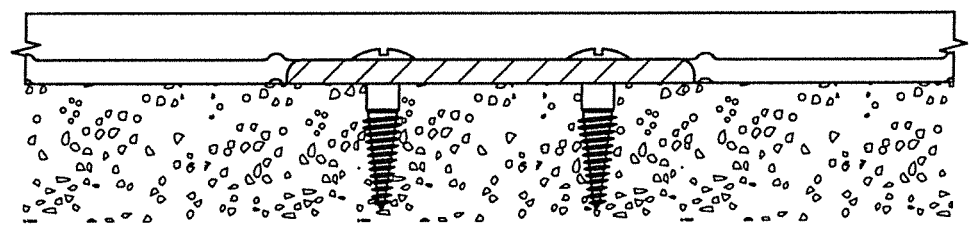
FIG. 21B is a side elevation view showing the plate of FIG. 16 in a lowered position.

The malleable petals or tabs 58 initially extend or curve downwardly toward the skull 16, as shown in FIGS. 19A, 20A, and 21A. When the plate 12A is lowered, the malleable petals 58 are substantially flush with the skull 16 and provide a smooth interface between the skull and the plate, as seen in FIGS. 19B, 20B, and 21B.

When the plate assembly 10, 10A is in the lowered or down position, the plate 12, 12A should interface securely with the patient's skull, without rocking or motion when a force is applied to the patient's overlying scalp. With traditional prior art cranioplasty plates, this securement is achieved by a plate that has a contour conforming well to the contour of the patient's skull, with stability achieved by placing many bone screws around the circumference of the plate implant. The bone screws also insure a substantially flush interface between the edge of the implant and the patient's skull so as to minimize the risk of scalp skin breakdown over any raised plate edge. However, the requirement to place numerous screws increases the duration of the surgical procedure and increases the surgeon's work load during the operation.

Also, because cranial plates are typically placed during urgent or emergency surgical procedures, "off-the-shelf" plate implants must be used, since there is insufficient time to fabricate a custom fit plate. Inevitably, these "off-the-shelf" implants have a contour that does not precisely match the contour of the patient's skull. The three-point fixation cranial plate assembly 10A shown in FIGS. 16-21 overcomes this prior art problem via the malleable, tapered petals 58 which provide a smooth interface with the skull surface while also allowing the plate 12A to be lowered through a single, small incision providing access to the ratchet wheel 38A. When the plate 12A is in the lowered position, the three equal-distant rigid extensions or tabs 56 are secured in position on the skull 16 via the retracted strut 20A. The tapered edges of the petals 58 insure a smooth circumferential interface between the plate 12A and the skull surface, even when there are surface contour discrepancies between the patient's skull and the assembly 10A. Positional differences across adjacent flange petals will be minimal, and not perceptible when the scalp is re-positioned over the top of the assembly 10A.

The strut blocks 60 may be constructed of plastic or other semi-malleable material. Each strut block 60 includes a slot 62 which can be slid over the rigid mounting tabs 57, as seen in FIG. 17A and the strut 20A so that the strut is received in a guide channel 64 of the strut block 60. After the assembly 10A is installed, the scalp can be closed over the implant 10A using standard surgical techniques.

As described for the plate assembly 10, the surgeon uses a template to trace the outline of the skull opening 48 that will be created, and select the appropriate size implant plate assembly. The time required to trace the skull opening and position, and secure the assembly 10A requires additional surgical time compared to a standard craniectomy procedure. That additional time will normally amount to less than 5 minutes.

After the brain swelling has dissipated (approximately two weeks post-operation) the plate 12A will be moved into the downward position using the same ratcheting technique described in the assembly 10. This can be performed in the outpatient clinic. Local anesthesia will be injected and a small incision (less than 1 cm) made over the central circular ratchet housing. The surgeon will use a hand-held ratchet rotator (e.g. hexagonal wrench) to rotate the ratchet 38A and pull the three contraction constructs 32A, 36A centrally, thus pulling the plate 12A downward until it is flush with the skull 16. During the maneuver the surgeon will exert gentle manual downward pressure on the plate 12A with the contralateral hand. Once the plate 12A is secured in the downward position the incision is sutured closed. The entire procedure time is estimated to be less than 10 minutes.

The assembly 10A has several advantages over the assembly 10, including: (1) improved positional stability in the final down position; (2) simplified and more rapid surgical implantation technique due to fewer connection points (approximately 80% time reduction in securing the assembly to the skull, and less than 5 minutes added to the standard craniectomy surgical procedure); and (3) simplified and less costly manufacturing due to fewer parts.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A cranioplasty plate assembly, comprising:
a plate to cover a skull opening and having opposite upper and lower surfaces and a perimeter edge;
a ring adapted to be fixed to the skull;
a plurality of struts, each having opposite inner and outer ends attached to the plate and to the ring for movement between a raised position to maintain the plate at a spaced distance above the skull and a lowered position for positioning the plate adjacent the skull; and
a contraction system to move the inner ends radially inwardly towards the center of the plate, wherein the contraction system includes a plurality of wires connected to the inner ends of the struts and a spool to wind the wires.

2. The cranioplasty plate assembly of claim 1 wherein the outer ends of the struts are pivotally attached to the ring.

3. The cranioplasty assembly plate of claim 1 wherein the inner ends of the struts are slidably slidable mounted to the plate.

4. The cranioplasty assembly plate of claim 1 wherein the spool is ratcheted.

5. The cranioplasty assembly plate of claim 1 wherein the spool includes a pawl with a plurality of teeth, and a catch to engage one of the teeth.

6. A method of protecting the brain following removal of a portion of the skull to form a skull opening, the method comprising:
fixing a ring to the skull such that the ring extends around the skull opening, the ring having an adjustable plate positioned over the skull opening and spaced from the brain; and
lowering the plate relative to the ring as brain swelling decreases;
wherein the plate lowering step includes adjustment of a contraction system; and wherein the adjustment includes rotation of a central wheel to retract struts extending between the plate and the ring.

7. The method of claim 6 wherein the adjustment includes actuation of a motor to retract struts extending between the plate and the ring.

8. The method of claim 6 further comprising preventing lateral shifting of the plate by tensioning a plurality of radially spaced cables attached to the plate.

9. The method of claim 6 further comprising preventing accidental downward movement of the plate by supporting the plate with a plurality of radially spaced struts.

10. An adjustable plate assembly for use following a craniotomy to form a skull opening which exposes a portion of the brain, comprising:
a ring adapted to be attached to the skull so as to extend around the opening;
a plate adjustably mounted to the ring and being movable between a raised position spaced above the ring and a lowered position substantially flush with the ring;
a plurality of extendable and retractable struts extending between the plate and the ring to position the plate in a selected position relative to the ring, wherein each strut has an outer end pivotally connected to the ring and an inner end slidably mounted to the plate, and wherein the inner end of each strut is attached to a cable, and the cable is connected to a wheel which rotates to retract the cable and the strut.

11. The adjustable plate assembly of claim 10 wherein the wheel includes teeth and a catch to engage the teeth to prevent reverse rotation of the wheel.

12. The adjustable plate assembly of claim 10 further comprising an actuator connected to the struts to move the struts between the raised and lowered positions.

13. The adjustable plate assembly of claim 10 further comprising a plurality of cables extending between the plate and the ring to prevent lateral movement of the plate relative to the ring when the plate is in the raised position.

14. A cranioplasty plate assembly, comprising:
a plate to cover a skull opening;
three mounting blocks adapted to be secured to the skull adjacent a skull opening; three strut systems forming a tripod having outer ends connected to the mounting blocks and inner ends retractably joined at an apex; and
the plate having a perimeter edge with tapered petals to provide a transition between the plate and the skull when the plate is lowered from a raised position above the skull to a lowered position adjacent the skull; and
wherein the plate includes three rigid extensions adjacent the perimeter and the mounting blocks.

15. The cranioplasty plate assembly of claim 14 wherein the petals are malleable.

16. The cranioplasty plate assembly of claim 14 further comprising a contraction system to contract the struts and thereby move the plate from a raised position to a lowered position.

17. The cranioplasty plate assembly of claim 14 further comprising three strut blocks, each adapted to receive a perimeter edge of the plate and one of the struts during installation of the plate onto the skull.

18. The cranioplasty plate assembly of claim 14 wherein the petals are angled downwardly toward the skull when the plate is in a raised position and are substantially flush with the skull when the plate is in a lowered position.

* * * * *